United States Patent
Khuri-Yakub et al.

(10) Patent No.: US 6,250,161 B1
(45) Date of Patent: *Jun. 26, 2001

(54) ULTRASONIC PHOTORESIST PROCESS MONITOR AND METHOD

(75) Inventors: Butrus T. Khuri-Yakub, Palo Alto; Susan Morton, Stanford; F. Levent Degertekin, Millbrae, all of CA (US)

(73) Assignee: Board of Trustees of the Leland Stanford Junior University, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/116,649

(22) Filed: Jul. 16, 1998

Related U.S. Application Data

(63) Continuation-in-part of application No. 08/943,575, filed on Oct. 3, 1997, now Pat. No. 6,026,688.

(51) Int. Cl.$^7$ .................................................. G01N 29/00
(52) U.S. Cl. ............................................................ 73/627
(58) Field of Search ............................ 73/627, 628, 629, 73/597, 645

(56) References Cited

U.S. PATENT DOCUMENTS

| | | |
|---|---|---|
| 4,625,556 | 12/1986 | Sukahara et al. ..................... 73/602 |
| 4,647,172 | 3/1987 | Batchelder et al. .................. 354/298 |
| 4,977,330 | 12/1990 | Batchelder et al. .................. 250/560 |
| 5,052,227 | 10/1991 | Le Floc'H et al. ..................... 73/644 |
| 5,240,552 | 8/1993 | Yu et al. ............................. 156/636 |
| 5,271,274 | 12/1993 | Khuri-Yakub et al. ................ 73/597 |
| 5,438,872 | 8/1995 | Kobayashi et al. .................... 73/597 |
| 5,469,742 | 11/1995 | Lee et al. .............................. 73/597 |
| 5,661,241 | 8/1997 | Harth, III et al. ..................... 73/622 |
| 5,672,830 | 9/1997 | Rogers et al. ......................... 73/597 |
| 5,996,415 | * 12/1999 | Stanke et al. ......................... 73/597 |
| 6,026,688 | * 2/2000 | Khuri-Yakub et al. ................ 73/597 |

OTHER PUBLICATIONS

Ballantine, David S., Jr. et al.; "Use of Saw Devices to Monitor Visco–Elastic Properties of Materials", *IEEE* 1988, pp. 559–562.

Ballantine, D.S. Jr., et al.; "Acoustic Wave Sensors: Theory, Design, and Physico–Chemical Applications", *Academic Press*, Chapter 4, pp. 154–167.

* cited by examiner

Primary Examiner—Richard A. Moller
(74) Attorney, Agent, or Firm—Flehr Hohbach Test Albritton & Herbert LLP

(57) ABSTRACT

There is provided a monitor and method for monitoring the condition of a photoresist film on a wafer in which the phase of high frequency ultrasonic pulses reflected from the wafer/photoresist interface provides an indication of the condition of the photoresist film.

4 Claims, 6 Drawing Sheets

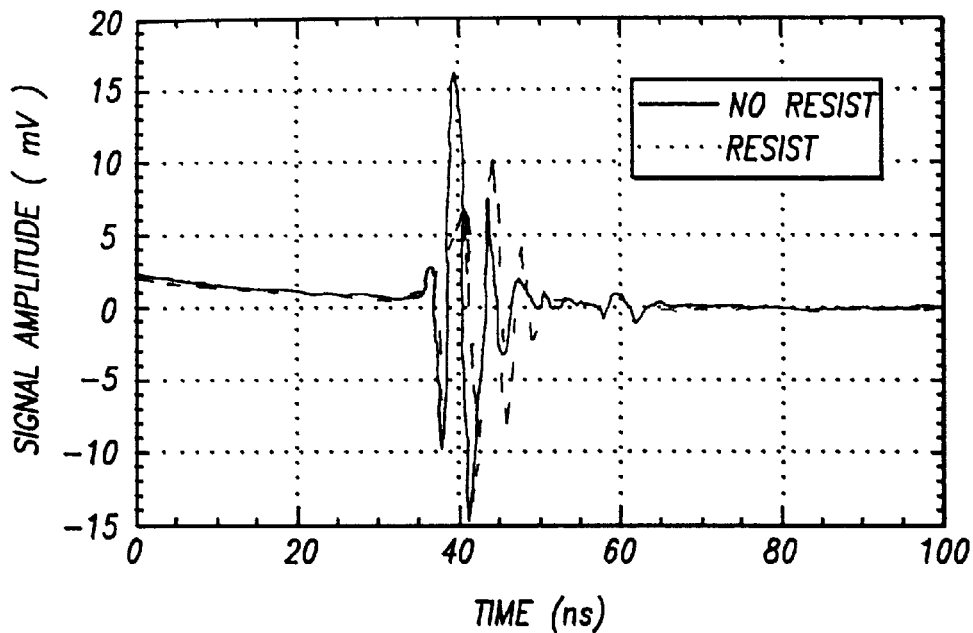
FIG.—5
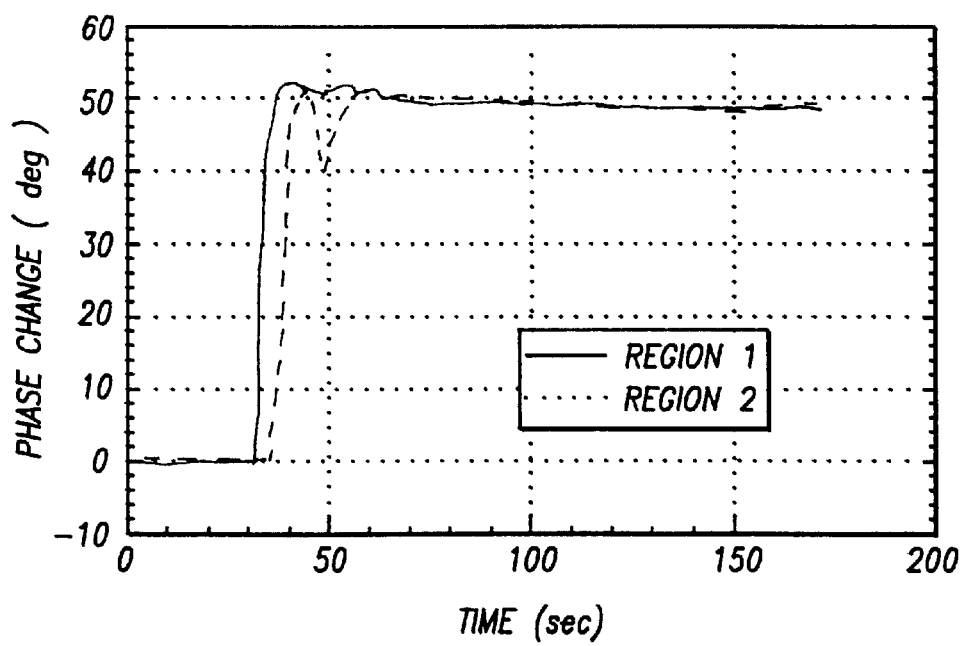
FIG.—6

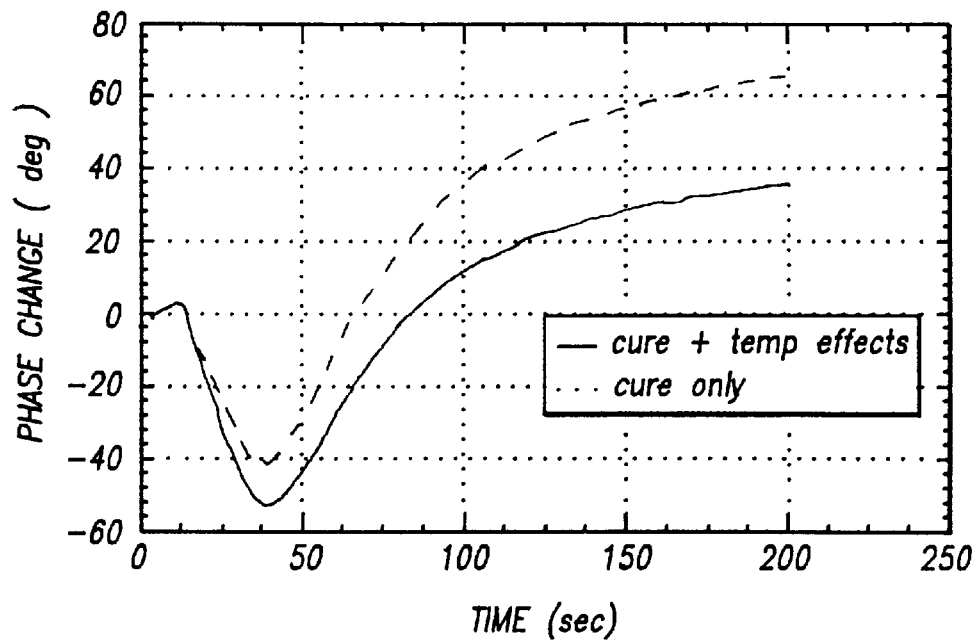
FIG.—7
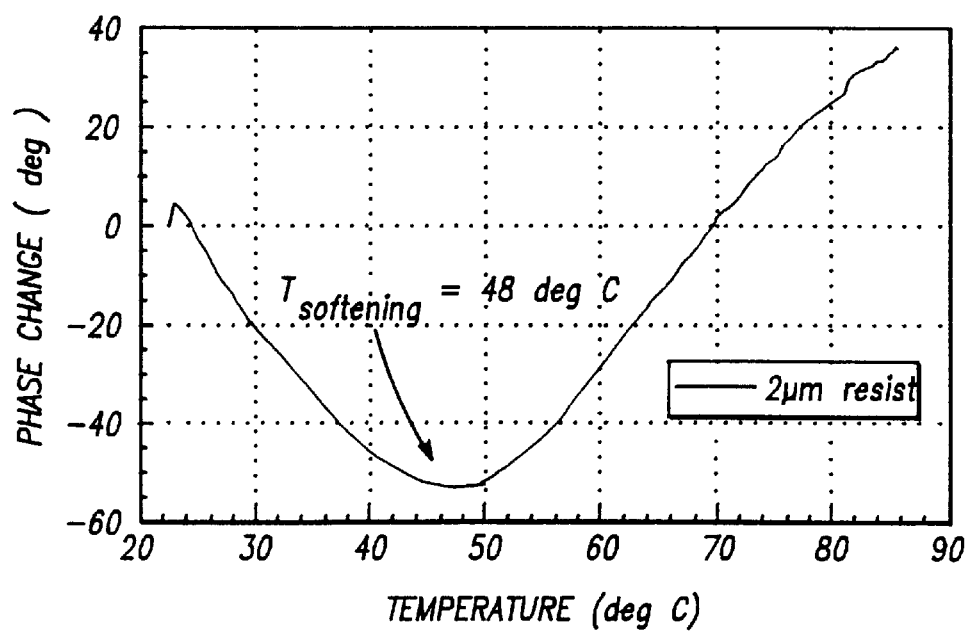
FIG.—8

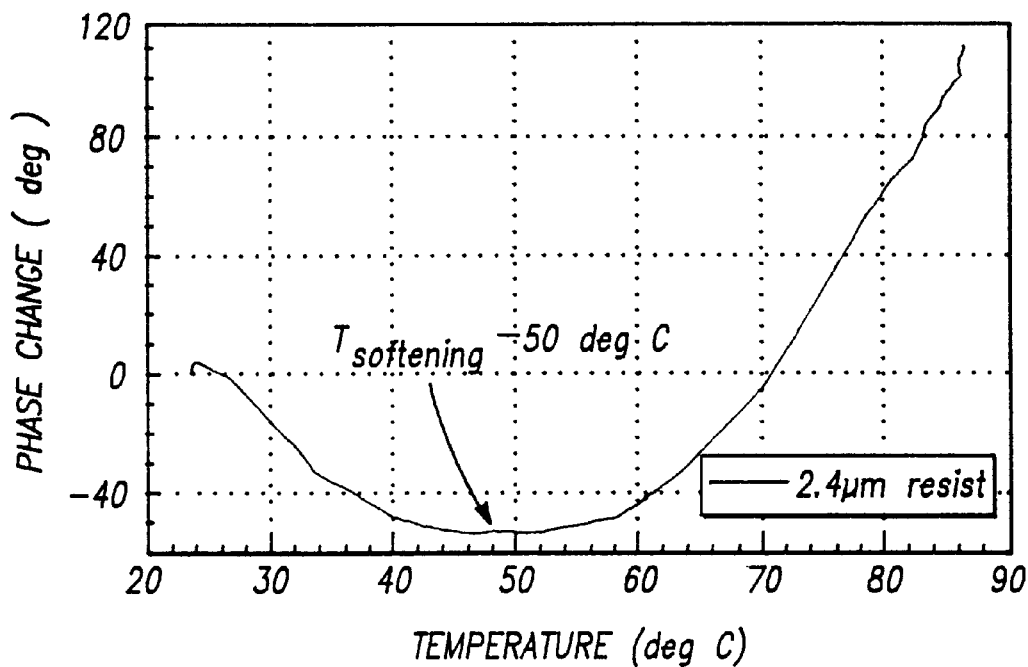
FIG.—9

ULTRASONIC PHOTORESIST PROCESS MONITOR AND METHOD

RELATED APPLICATION

This application is a continuation-in-part of application Ser. No. 08/943,575 filed Oct. 3, 1997, now U.S. Pat. No. 6,026,688.

GOVERNMENT SUPPORT

The research which led to this invention was funded by the Defense Advanced Research Project Agency of the Department of Defense and monitored by the Air Force Office of Scientific Research under Grant No. F49620-95-1-0525.

BRIEF DESCRIPTION OF THE INVENTION

The present invention relates generally to an ultrasonic photoresist process monitor and method and more particularly to an in situ monitor which monitors the processing of photoresist film, particularly pre-exposure bake conditions and film thickness.

BACKGROUND OF THE INVENTION

In the manufacture of integrated circuits the various circuit components are defined by using a photoresist layer which is applied to the surface of a semiconductor wafer, exposed and developed. The photoresist is applied to the surface of the wafer by applying a few drops of liquid resist onto a spinning wafer to obtain a photoresist film of predetermined thickness. The photoresist liquid film is prebaked to remove any excess solvent that is initially added to the resist as well as to anneal the polymer film, allowing the resin molecules to relax into their lowest energy state. This thin film of resist is typically on the order of 1–2 μm thick. The film thickness changes about 0.5 μm during prebake.

If the solvent is not fully evaporated or if the prebake time is too long, then the feature size of the developed film may not be as small as expected. It is important when heating the resist for prebake that the temperature of the film reach and exceed the glass transition temperature ($T_g$) in order to facilitate the removal of solvent and formation of polymer chains. It is important that the bake time be controlled. If the glass transition temperature is measure then the processing time may be easily controlled. In practice, a calibration run will provide the time T, after $T_g$ is reached, required to complete the prebake cycle. It is also important to monitor the postbake or cure process after exposure and before development so that the wafer is not heated above the softening temperatures where features would be altered.

Several techniques are available to measure $T_g$ but none of them have been applied in situ for endpoint detection of photoresist softbake. There has been research in endpoint detection of the prebake process. T. E. Metz et al. "Process Module Metrology Control and Clustering", SPIE, Vol. 1594, 1991, pp. 145–152, performed real-time measurement of resist film thickness on silicon wafers using multi-wavelength reflection interferometry. They determined resist thickness vs. spin and bake time. This method was used to monitor non-uniformities for statistical process control.

There is a need for in situ photoresist monitoring as feature size surpasses sub-quarter micron size since it is expected that the resist materials will be more sensitive to process conditions such as temperature and time.

The development of the film after it has been laid down, prebaked and exposed involves the selective dissolution of exposed areas of positive tone photoresist (unexposed areas of negative resist) by applying a basic solution to the wafer and spinning. It is important to determine when all of the exposed resist is removed so that the wafer can be immediately advanced to the next processing step, thereby saving time and increasing throughput.

OBJECTS AND SUMMARY OF THE INVENTION

It is a general object of the present invention to provide an in situ photoresist process monitor and method for monitoring photoresist process conditions.

It is another object of the present invention to provide an ultrasonic photoresist process monitor.

It is a further object of the present invention to provide a photoresist process monitor which has fast response and provides repeatable process conditions.

It is a further object of the present invention to provide a monitor which measures glass transition temperature of a photoresist during its pre-exposure bake.

It is a further object of the present invention to provide an ultrasonic monitor which measure the glass transition temperature of photoresist during its pre-exposure bake (prebake), and also during post-exposure baking.

The monitor of the present invention determines the glass transition temperature, $T_g$, of a photoresist film during prebake processing by measuring the change of phase of a high frequency ultrasonic pulse as it is reflected from the interface between the wafer and the photoresist film.

It is a further object of the present invention to provide a photoresist monitor which measures the photoresist film thickness during development and determines when the exposed film has been removed.

The photoresist process monitor includes a transducer which transmits ultrasonic waves into the underside of a wafer and receives ultrasonic waves reflected from the interface between the wafer and a photoresist film carried on the other surface of the semiconductor wafer. The monitor provides an output signal representative of the phase difference between two successive reflected waveforms from the silicon photoresist interface. The output signal is processed to provide an indication of glass transition temperature and/or film photoresist thickness.

BRIEF DESCRIPTION OF THE DRAWINGS

The foregoing and other objects of the invention will be more clearly understood from the following description when read in connection with the accompanying drawings of which

FIG. 5 illustrates the reflected ultrasonic pulses with and without photoresist removal.

FIG. 6 shows the phase change during resist removal at two points on a wafer.

FIG. 7 shows the phase change vs. time of cure with temperature effects (solid line) and after temperature effects have been inverted out (dashed line).

FIG. 8 shows phase change vs. temperature during prebake for 2 μm resist thickness.

FIG. 9 shows phase change at vs. temperature during prebake for 2.4 μm resist thickness.

DESCRIPTION OF PREFERRED EMBODIMENT

Figure 1:
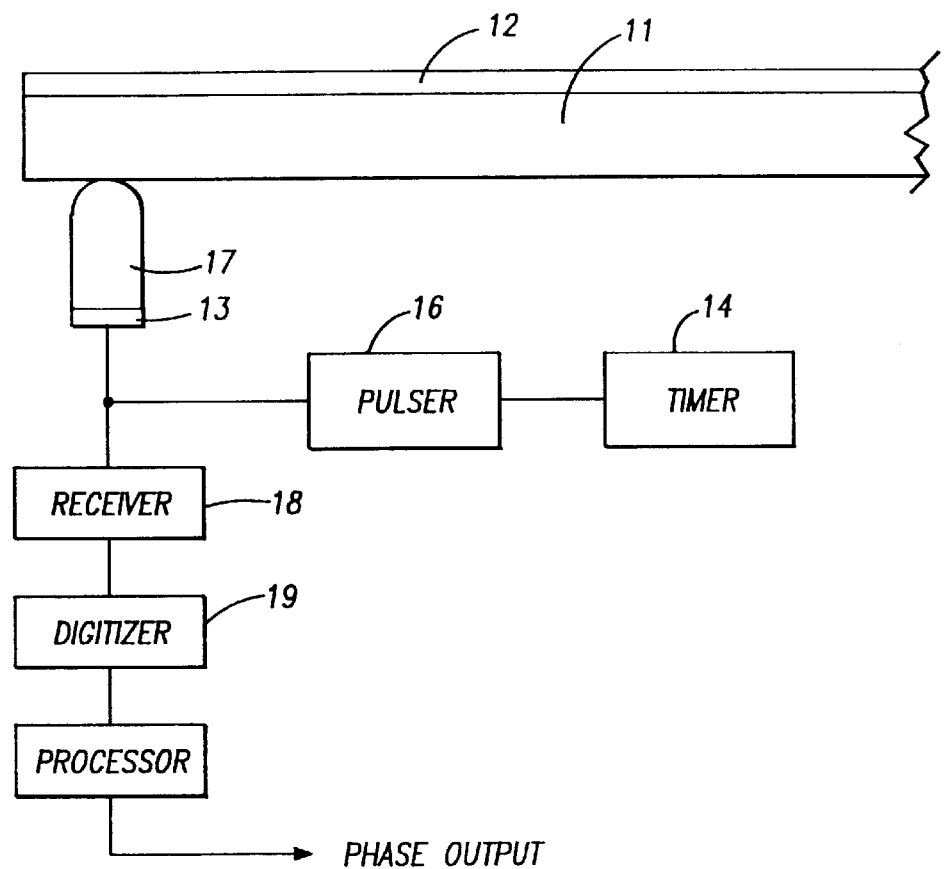
FIG. 1 is a diagrammatic illustration of an in situ photoresist process monitor in accordance with the present invention.
Figure 2:
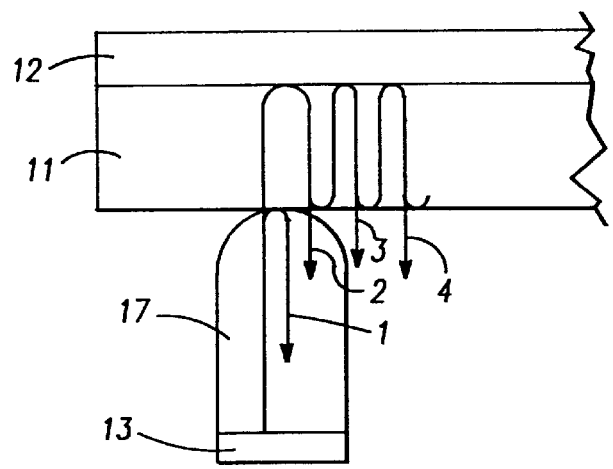
FIG. 2 illustrates the path of the ultrasonic waves applied to a wafer with a hotoresist film.
Figure 3:
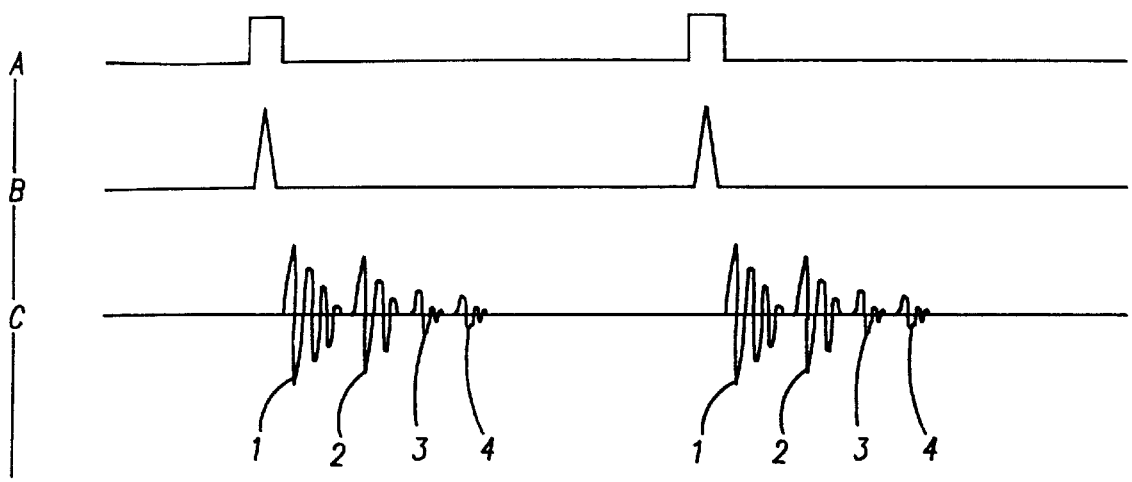
FIGS. 3A–3C show the generation of ultrasonic pulses applied to the transducer FIG. 1), and the pulses reflected from the transducer wafer interface and from the wafer photoresist film interface.
Figure 4:
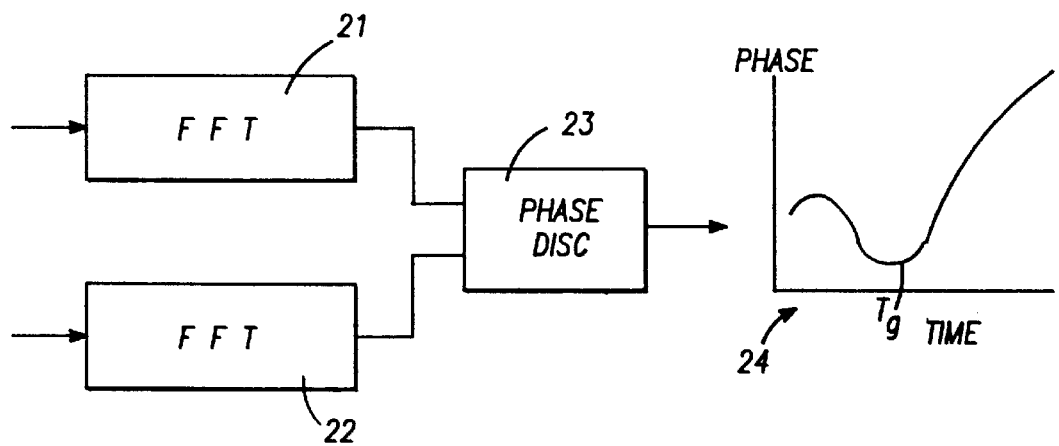
FIG. 4 schematically shows a processing circuit for providing the measurement of phase differences between reflected pulses.

In FIG. 1 a wafer 11 is shown with a photoresist film 12. Ultrasonic waves are used to determine changes in the photoresist film during the prebake process. The ultrasonic waves or pulses are generated by a piezoelectric transducer 13. High voltage pulses are applied across zinc oxide piezoelectric transducer 13 which in this example resonates at 260 MHz. The resonant frequency is determined by the thickness of the transducer. The transducer causes mechanical displacement which launches longitudinal acoustic waves. A timer 14 applies timing pulses (FIG. 3A) to a pulser 16. The pulser 16 applies the high voltage pulses (FIG. 3B) across the piezoelectric transducer 13. The longitudinal waves excited by the transducer are coupled into the underside of the wafer by direct contact through a sapphire buffer rod 17. These waves are reflected from the silicon/photoresist interface and from the buffer rod wafer interface. The reflection of the pulses directly from this buffer rod wafer interface is shown at 1, in the enlarged view of FIG. 2. The waves reflected from the interface are shown at 2 (FIG. 2). Pulses reflected by the interface and reflected by the underside of the wafer and again reflected by the interface are shown by at 3 (FIG. 2) and further multiply reflected pulses are shown at 4 (FIG. 2). It is understood that additional multiply reflected pulses are generated but not shown. The transducer serves as receiver for the reflected ultrasonic waves or pulses. The output signal from the transducer is received by a receiver 18, digitized by a digitizer 19, such as a HP542508 digital oscilloscope at 1 G samples/second. The digitized waves are applied to a processor which provides an output signal representative of the phase difference between waves 2 and 3. A suitable processor circuit is shown in FIG. 4 as including fast Fourier transforms 21 and 22 whose output is applied to a phase difference detector 23 which provides the phase of the reflection coefficient as output signal 24.

The phase of the reflection coefficient of a plane wave incident from a medium (wafer) on a layer (photoresist) is governed by $$R = \left[ \frac{\left(1 - \frac{z_1}{r_3}\right)\cos k_2 L + j\frac{z_2}{z_3}\sin k_2 L}{\left(1 + \frac{z_1}{z_3}\right)\cos k_2 L + j\frac{z_2}{z_3}\sin k_2 L} \right] \quad (1)$$

In this equation, R is the reflection coefficient, $z_1$ is the acoustic impedance of silicon, $z_2$ is the acoustic impedance of the photoresist, $z_3$ is the acoustic impedance of air, L is the photoresist thickness, and $k_2$ is the velocity of sound in the photoresist. During prebake there are changes in the thickness of the resist film and the velocity of the wave in the film and the film density.

There will also be a phase change in the reflected signal as the wafer changes temperature. During the prebake, the wafer temperature typically increases from room temperature to 90° C. The relation from which the one-way phase change can be calculated or a given temperature change is given in Equation 2.

$$\Delta\Phi(T) = 2\pi f d \left[ \frac{1}{V(T_0)(1 - k_v(T - T_0))} - \frac{1}{(v(T_0))} \right] \quad (2)$$

Where d is the thickness of the silicon wafer, f is the frequency, v(T) is the bulk velocity in silicon at temperature T, $T_0$ is room temperature, 25° C., and $k_v$ is the temperature sensitivity coefficient of the wave velocity. It has been shown experimentally for silicon that this relationship is linear within the temperature range of the bake. This relation was used to remove the effects of temperature on the measurements. The calculated change is multiplied by two to compensate for wave travel to and from the interface.

To evaluate the sensitivity of the phase measurement, the change in phase of a reflected signal was determined as a layer of photoresist was removed with acetone. A clean 8" silicon wafer was spin-coated with a 2.4 μm layer of Shipley 1813 resist and prebaked for 90 seconds on a hotplate at 90° C. The wafer was supported a sapphire rod 17 with a transducer 13 and two spaced quartz support pins. The reflected ultrasound signal was monitored for about 1–2 minutes prior to removing the resist in order to obtain the measurement noise level. The noise was about 0.2 degrees peak to peak with a standard deviation of 0.07 degrees. Acetone was then applied to the wafer to remove the resist layer, and the signal was continuously monitored until the phase stabilized. This experiment was repeated at other points on the same wafer. FIG. 5 shows the reflected high frequency signal from the silicon/resist interface before and after the resist was removed from the wafer. There is a substantial phase difference.

FIG. 6 shows the measured phase change as a function of time at 260 MHz. A 48 degree change in phase was measured when the resist was removed, agreeing well with theory. The experiment was repeated on another part of the wafer with similar results plotted on the same graph in FIG. 6. The variations in phase directly following resist removal were attributed to temperature changes associated with solvent evaporation.

Thus, the phase change is an indication of the complete removal of the photoresist film during development. This can be used to monitor photoresist film development by focusing the transducer at a predetermined test area during photoresist dissolution and measuring the reflection phase change.

Next, the phase change was measured during resist prebake to look for a significant and repeatable trend in the entire phase change that could be used to determine the state of cure at a given time. The expected change in phase during the bake is a steady increase due to decreasing thickness and increasing density. The actual value of phase change depends on the starting and ending point conditions of the film, including thickness, density, and velocity. This excludes the effects of wafer heating, which is expected to be linear (Equation 2), as well as the changes in the elastic properties of the resist due to its softening.

An 8" wafer was cleaned and the phase measured as the bare wafer was heating. In this way, the slope of the linear relationship between phase and temperature was obtained. This was later used to remove the temperature effects from the total phase change during cure. Next, a wafer was coated with Shipley 1813 resist at a spin speed of 3000 rpm. The coated wafer was immediately placed on top of the buffer rod and two quartz pins and a heating lamp was turned on to begin the prebake. The reflected waveforms and temperature data were obtained once every 3 second for about 200 seconds, well beyond the usual bake time of 90 seconds. The total phase change as a function of time and temperature was obtained with the monitor system shown in FIG. 1. The temperature effects were subtracted.

The measured phase as a function of time of cure is plotted in FIG. 7, both with and without the temperature effect. The phase is plotted at 280 MHz since the measurement sensitivity was highest at this point. There is an initial decrease in phase followed by a rapid increase which eventually levels off. It is believed that the initial decrease in phase is due to the film softening during heating. Also, the rapid increase in phase that follows the minimum is likely due to the onset of solvent evaporation. This occurs after the resist has softened, allowing for the diffusion of solvent molecules that facilitates evaporation.

FIG. 8 shows the change in phase for a 2 μm thick resist, this time plotted as a function of temperature. There is a repeatable phase minimum occurring at about 48° C. It is believed that the temperature of this minimum represents the characteristic glass transition temperature ($T_g$) of the resin/solvent mixture. This is important because it indicates the point at which significant evaporation and polymer relaxation occur and, therefore, the point at which significant prebaking begins. The baking time can be timed from this point. It also can provide a temperature calibration point that can be used in determining the temperature profile of a given prebake cycle. The temperature uniformity is known to affect the final critical dimension (CD) of a feature that is being processed. For both FIGS. 7 and 8, the final thickness of the resist after prebake was 2 μm. FIG. 9 shows the phase as a function of temperature for a 2.4 μm resist.

Figure 10:
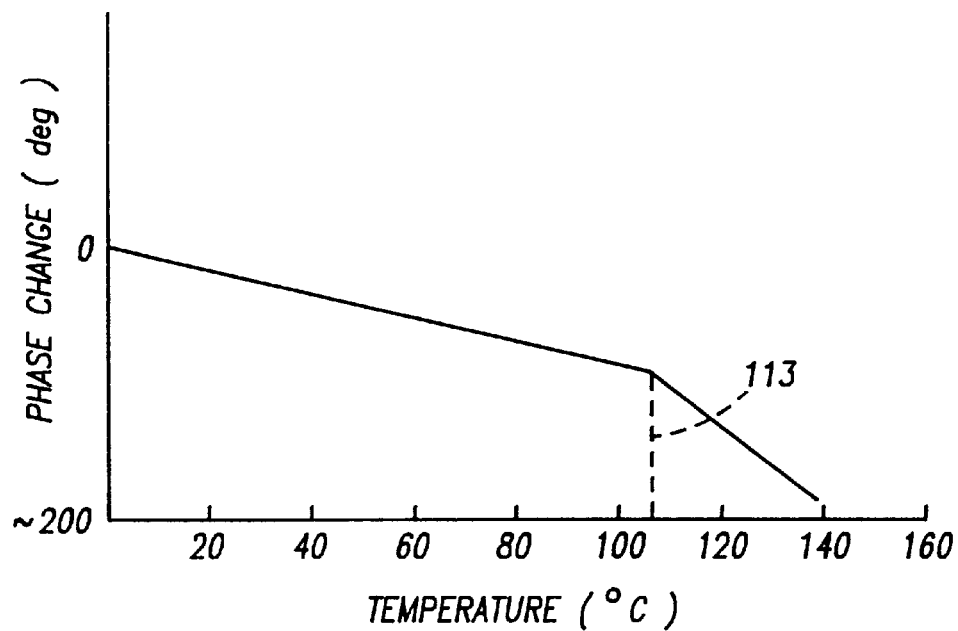
FIG. 10 shows phase change as a function of temperature for postbake.

We expect that the phase change during postbake will be different than that during prebake. The phase will decrease linearly as the wafer and resist heat up. Once the resist reaches the glass transition temperature of the polymer, about 113° C. for Shipley 1813 resist, we expect a slope change due to softening of the photoresist film. This change in slope can be detected and used to control the postbake to prevent softening when features would be altered. This should be a more rapid decrease in slope to a more negative value as shown in FIG. 10 at temperature 113° C.

Figure 11:
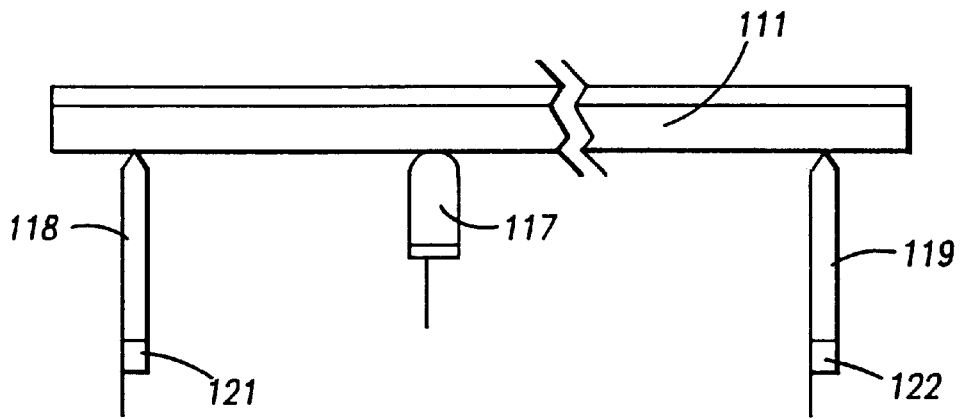
FIG. 11 schematically shows another embodiment of the invention.

The buffer rod can be used as part of the support structure which keeps the wafer from directly contacting the previous chunk. In another embodiment the wafer can be supported by spaced quartz rods and the buffer rod. The quartz rods may form part of an acoustic temperature monitor. Referring to FIG. 1, the wafer 111 is supported on buffer rod 117 and spaced quartz rods 118 and 119. Piezoelectric transducer 121 applies acoustic waves to the rod 118 and transducer 122 receives acoustic waves from the rod 119. Low frequency longitudinal acoustic waves in the rod 118 are coupled to the wafer where they generate Lamb waves. The Lamb waves are received by the rod 119 and transmitted to the transducer 122. The acoustic waves have velocities which depend on temperature. Thus the time it takes a wave to travel between rods 118 and 119 is a measure of velocity which is dependent on temperature. Wafer temperatures monitor is described in U.S. Pat. No. 5,469,742, incorporated herein by reference. Thus the monitor shown in FIG. 11 can be used as a monitor for photoresist processing time and temperature. The minimum temperature at the phase (FIG. 8) can be used to calibrate the acoustic temperature sensor.

There has been provided an ultrasonic monitor which measures changes in the phase of ultrasound waves reflected from the interface of a photoresist film with the semiconductor wafer. The monitor can be used to measure the thickness of the photoresist film and to indicate removal of the film from predetermined areas of the wafer.

The monitor and method can also measure glass transition temperature during prebaking of the photoresist by monitoring the phase of a high frequency ultrasonic reflection from the silicon/resist interface. Since it is at the glass transition temperature that the resist softens and the diffusion and evaporation of the solvent molecules in the resist become significant, a measure of the glass transition temperature allows us to determine resist cure state, both during prebake and postbake.

What is claimed is:

1. A photoresist process monitor for monitoring the removal of a photoresist film on one major surface of a semiconductor wafer comprising:

a buffer rod having one end in contact with the other major surface of said semiconductor wafer;

a piezoelectric transducer for generating ultrasonic pulses secured to the other end of the buffer rod whereby the rod transmits the ultrasonic pulses from the piezoelectric transducer into the wafer and receives ultrasonic pulses reflected from the wafer/photoresist interface to generate output signals;

a means for receiving which is configured to process the output signals from said piezoelectric transducer and to generate an output indicative of the removal of the photoresist film from the one major surface responsive to changes in phase of the reflected pulses.

2. A photoresist process monitor as in claim 1 in which said means for receiving and processing the output signals includes a digitizer and fast Fourier transforms.

3. A photoresist monitor as in claim 2 including a pulser for applying excitation pulses to said piezoelectric transducer.

4. The method of monitoring for removal of a photoresist film from one major surface of a wafer comprising:

transmitting into the wafer from the other major surface high frequency ultrasonic pulses which are reflected from the major surface, receiving said reflected pulses and providing output signals, measuring changes in phase of the high frequency ultrasonic pulses reflected from the major surface, and processing said phase changes to provide an indication of the removal of said photoresist film from the major surface.

* * * * *